(12) United States Patent
Dual et al.

(10) Patent No.: US 7,691,570 B2
(45) Date of Patent: Apr. 6, 2010

(54) CHEMICAL ANALYSIS USING DYNAMIC VISCOMETRY

(76) Inventors: Jürg Dual, Waldegg 10A, 8126 Zumikon (CH); Lukas Bestmann, Freiestrasse 43, 8406 Winterthur (CH); Klaus Häusler, Sillerwies 10, 8053 Zürich (CH)

( * ) Notice: Subject to any disclaimer, the term of this patent is extended or adjusted under 35 U.S.C. 154(b) by 476 days.

(21) Appl. No.: 10/578,942

(22) PCT Filed: Nov. 5, 2004

(86) PCT No.: PCT/CH2004/000675

§ 371 (c)(1), (2), (4) Date: Jan. 11, 2007

(87) PCT Pub. No.: WO2005/045068

PCT Pub. Date: May 19, 2005

(65) Prior Publication Data

US 2008/0026369 A1   Jan. 31, 2008

(30) Foreign Application Priority Data

Nov. 6, 2003   (CH) ..................................... 1923/03

(51) Int. Cl.
*C12Q 1/68* (2006.01)
(52) U.S. Cl. ......................................................... 435/6
(58) Field of Classification Search ........................ None
See application file for complete search history.

(56) References Cited

U.S. PATENT DOCUMENTS

| | | | | |
|---|---|---|---|---|
| 3,930,402 A | * | 1/1976 | Detmar et al. | 73/54.09 |
| 4,889,816 A | * | 12/1989 | Davis et al. | 436/518 |
| 4,920,787 A | * | 5/1990 | Dual et al. | 73/54.41 |
| 5,486,335 A | * | 1/1996 | Wilding et al. | 422/55 |
| 5,494,639 A | * | 2/1996 | Grzegorzewski | 422/82.01 |
| 5,606,045 A | * | 2/1997 | Dandliker et al. | 536/25.32 |
| 5,837,885 A | * | 11/1998 | Goodbread et al. | 73/32 A |
| 6,168,948 B1 | * | 1/2001 | Anderson et al. | 435/287.2 |
| 6,174,670 B1 | | 1/2001 | Wittwer et al. | |

FOREIGN PATENT DOCUMENTS

| | | |
|---|---|---|
| DE | 36 15 553 A1 | 11/1987 |
| SU | 1289870 A1 | 2/1987 |
| WO | 95/24630 A1 | 9/1995 |

OTHER PUBLICATIONS

Goodman, A., et al., "Effect of Length, Topology, and Concentration on the Microviscosity and Microheterogeneity of DNA Solutions," *Journal of Molecular Biology*, Oct. 18, 2002, pp. 199-215, vol. 323, No. 2, London, GB, XP004449864.

Database WPI Week 1987, *Derwent Publications Ltd.*, London, GB; AN 1987-270360 XP002315289.

Suh, D., et al., "Criteria for the Mode of Binding of DNA Binding Agents," *Bioorganic & Medicinal Chemistry*, Jun. 1995, pp. 723-728, vol. 3, No. 6, XP002315287.

Parodi, S., et al., "A Circular Channel Crucible Oscillating Viscometer: Detection of DNA Damage Induced in Vivo by Exceedingly Small Doses of Dimethylnitrosamine," *Journal of Molecular Biology*, 1981 pp. 501-521, vol. 147, No. 4, United Kingdom, XP009042966.

Bernengo, J.C., et al., "An Automatic Recording Device For Zimm-Crothers Viscometer," *Review of Scientific Instruments*, 1973, pp. 311-313, vol. 44, No. 3, XP002315288.

* cited by examiner

*Primary Examiner*—Christopher M. Babic
(74) *Attorney, Agent, or Firm*—Sughrue Mion, PLLC (57) ABSTRACT

The invention relates to a method for determining the reactive state of a chemical reaction process in a reaction mixture (110), in particular an amplification reaction for nucleic acids. The method comprises a viscosity determination, which preferably uses a dynamic viscometer (1). The invention also relates to an improved dynamic viscometer (1) for carrying out said method. The viscometer is characterised by an appropriate choice of material for the resonator (101) and optimised geometric ratios.

21 Claims, 5 Drawing Sheets

CHEMICAL ANALYSIS USING DYNAMIC VISCOMETRY

TECHNICAL FIELD

The present invention relates to a method and an apparatus for determining the reaction status of a chemical reaction, in particular a reaction for amplifying nucleic acids.

PRIOR ART/BACKGROUND OF THE INVENTION

It is usually desired in chemical reactions to quantify the result of the reaction by measuring suitable variables or to follow the progress of the reaction by means of such a variable. A well-known example is following the changes in color of a colored indicator which has been added to a reaction mixture.

In a process for amplifying nucleic acids, in contrast to usual chemical reactions, a precursor is not converted into a completely different product, but one part of a molecule is copied with the aid of other precursors. In the specific case of methods for amplifying nucleic acids, especially the polymerase chain reaction (PCR), the result of the reaction is nowadays frequently quantified by staining with ethidium bromide and detecting the fluorescent signal. It has also been proposed to detect the hybridization process itself by fluorescence. Such a method is disclosed in U.S. Pat. No. 6,174,670. The detected fluorescent signal results from a fluorescence resonance energy transfer (FRET) between two fluorophores on excitation of the donor fluorophore with light. The DNA can be genotyped by analyzing specific melting and solidification curves.

Monitoring the progress of a reaction by fluorescence is relatively complicated, because a sensitive optical system must be provided for detection. In addition, such a method is costly to use because of the fluorescence markers necessary therefor.

It is also known to examine the progress of viscosity-altering reactions, e.g. polymerization reactions, by means of viscometry. A reaction is viscosity-altering if the viscosity of the product of the mixture of the products differs from the viscosity of the mixture of the precursors. The viscosity of the mixture will then approach the viscosity of the products as the reaction increasingly advances. Measurement of viscosity then provides a measure of the advancing of the reaction. The viscometers employed for this purpose are, however, ordinarily optimized for industrial production plants and unsuitable for examining small reaction volumes.

SUMMARY OF THE INVENTION

It is therefore an object of the present invention to provide a method for determining the reaction status of a chemical reaction process in a reaction mixture, where the chemical reaction process includes an amplification reaction for nucleic acids. The method is intended to be simple to carry out and cost-effective. This object is achieved by a method having the features of claim 1.

The method of the invention includes a determination of the viscosity of the reaction mixture. This can take place with a suitable viscometer, preferably with a dynamic viscometer. However, it is also possible to use another type of viscometer, e.g. a capillary viscometer as known in the art.

It is further intended to provide a method for determining the reaction status of a chemical reaction process in a reaction mixture which is particularly suitable for small sample quantities and can be carried out cost-effectively. This object is achieved by a method having the features of claim 5. This method is distinguished by the use of a dynamic viscometer and comprises the steps:

provision of the dynamic viscometer which comprises a resonator and at least a first transducer cooperating with the resonator, where the resonator is capable of a mechanical natural vibration with a characteristic frequency, and has a contact surface;

contacting the reaction mixture with the contact surface;

determining a measure of the viscosity by means of the dynamic viscometer.

It is a further object of the present invention to indicate an apparatus which is particularly suitable for determining the reaction status of a chemical reaction. This object is achieved by an apparatus having the features of claim 9.

Advantageous embodiments of the invention are indicated in the dependent claims.

In the method according to the present invention, the reaction status, especially the result, of a chemical reaction is determined. The chemical reaction preferably includes at least one reaction step in which an amplification of nucleic acids takes place. The method is distinguished by performing a measurement of the viscosity.

The method of the invention makes it possible to establish, very cost-effectively, whether and the extent to which an amplification has in fact taken place. This is based on the realization that virtually every amplification reaction leads to a viscosity alteration, e.g. a polymerase chain reaction (PCR), a ligase chain reaction (LCR) or a NASBA reaction (nucleic acid sequence based amplification). The corresponding methods are well known in the art.

The method of the invention makes it possible in particular to carry out very cost-effectively methods for screening for the presence of nucleic acids of particular organisms or for the presence of a mutation in the genetic material of an organism, especially of a microbial, plant or animal (including human) organism. For the last-mentioned application, the method preferably includes further analysis steps which allow the presence of a mutation in a nucleic acid to be determined.

In a preferred embodiment, the amplification reaction in this case includes an allele-specific amplification reaction as is well known in the art. An allele-specific amplification is an amplification in which the quantity of the nucleic acid fragments generated by the reaction depends on the absence or presence of the mutation on a target sequence initially present. The further analysis steps then preferably include a step in which the determined measure of the viscosity is compared with a previously measured or calculated reference standard, the result of this comparison enabling a decision to be made about the presence of the mutation.

The reaction process preferably includes at least one reaction step in which nucleic acid fragments are linked together, preferably in a form in which the fragments polymerize together. In a preferred embodiment, the linkage of target nucleic acid fragments takes place by means of linker oligonucleotides. The linker oligonucleotide is designed to hybridize with a first probe region near its 5' end on a first nucleic acid fragment and to hybridize with a second probe region near its 3' end on a second nucleic acid fragment. The linker oligonucleotides are preferably themselves linked by means of a ligase subsequent to such a hybridization process. This can take place in the form of an LCR. Before the linkage with the ligase it is optionally possible also for an elongation to take place with a polymerase without 3'→5' exonuclease activity, as is normally used in a so-called gap LCR. The linker oligonucleotide preferably includes a linker region which includes a repetitive arrangement of bases, e.g. a region of preferably 5 to 20 identical bases, e.g. T bases. The two probe regions, whose nucleotide sequences are preferably substantially complementary to one target sequence in each case, adjoin on both sides of this region. If the linkage of the linker oligonucleotides is to take place allele-specifically on a single nucleotide polymorphism (SNP, exchange of a single base at a mutation site), the linker oligonucleotide is preferably chosen so that a base, which preferably forms the 3' end of the linker oligonucleotide or is a few, preferably one or two, positions away from the 3' end, is complementary to the base of the target sequence at the mutation site.

The linker region and the adjoining regions are designed so that substantially no hybridization of both probe regions to a single nucleic acid fragment with the target sequence takes place, but so that preferably each of the probe regions hybridizes to a different nucleic acid fragment having the target sequence. In order for it to be possible for linkage by the ligase to take place, the 5' end of the linker oligonucleotide is preferably phosphorylated.

Thus, there is here firstly a linkage of target nucleic acid fragments by linker oligonucleotides, and secondly in addition a linkage of the linker oligonucleotides. The linkage may result in a linear macromolecule and/or a network. Concerning the terms "linear macromolecule" and "network", reference is made to the IUPAC Compendium of Chemical Terminology, 2nd edition (1997). Such an additional polymerization leads to a marked increase in viscosity as long as a sufficient quantity of precursor, i.e. a sufficient number of fragments of the target sequence, is present.

The viscosity is preferably determined using a dynamic viscometer, but can also be determined for example with a known capillary viscometer.

A dynamic viscometer means in connection with this document an apparatus which includes a resonator which is capable of a mechanical natural vibration, preferably a torsional vibration. The resonator has a contact surface which can be brought into contact with a fluid. The resonator, and thus the contact surface, can be stimulated to vibrate by means of a transducer, e.g. a piezo transducer or an electromagnetic transducer. The fluid on the contact surface will damp the vibration. A measure of the viscosity of the fluid can then be derived from the damping of the resonator. A quantitative determination of the viscosity is possible if the density of the fluid is known.

A dynamic viscometer is easy to use, cost-effective to produce and highly sensitive for small viscosity changes. Whereas dynamic viscometers are known per se, the method of the invention is distinguished by using the dynamic viscometer to obtain information about the reaction status through the viscosity. In contrast to methods like those typically employed for monitoring industrial polymerization reactions, the method of the invention is particularly suitable for applications in which the quantity of the reaction mixture is relatively small.

Various embodiments of dynamic viscometers are described in U.S. Pat. No. 4,920,787 and WO 95/24630. Explicit reference is made to the disclosure in these documents for the configuration of a dynamic viscometer.

A great advantage of using a dynamic viscometer in the method of the invention is the high sensitivity which can be achieved with dynamic viscometers. Even small viscosity changes, of the scale of a few percent or less, in small sample volumes can be detected with such a viscometer. The reaction mixture is preferably present in a sample chamber which comprises the contact surface of the resonator and whose volume is less than 1 milliliter, preferably less than 100 microliters, in an advantageous configuration less than 10 microliters. The volume of the sample chamber will ordinarily exceed 1 microliter; however, the volume may be below this value with an appropriate design of the viscometer. In order to enable such small sample volumes to be measured with sufficient sensitivity, the present invention also provides particular configurations of the viscometer.

The sample chamber is preferably at least partly delimited by capillary forces. It is thus very simple, in particular with small sample volumes, to bring an exactly defined region of the contact surface into contact with the reaction mixture, and hold it there during the measurement.

In the method of the invention it is possible for a reaction process to take place while the reaction mixture is present in the sample chamber of the viscometer, or the reaction mixture is introduced into the viscometer only after the reaction has taken place. Advantages accrue if at least part of the reaction process takes place while the reaction mixture is in contact with the contact surface, because elaborate sample transfers can then be omitted. This is an advantage in particular if the reaction process is a reaction for amplifying nucleic acids, because possible contamination is thus avoided and an elaborate manual step in the manipulation can be omitted. It is also possible by periodic measurement of the viscosity to follow the advance of the reaction directly. In this case, the contact surface is preferably formed by the inside of a glass tube, and a temperature-control element, e.g. a heating element or a Peltier element permitting both heating and cooling, is advantageously vapor-deposited on the glass tube.

The invention also relates to an apparatus for determining the reaction status of a viscosity-altering chemical reaction process in a reaction mixture. This apparatus is distinguished by comprising a dynamic viscometer with a torsional vibrator as resonator. In other words, the apparatus includes a resonator which has a contact surface and is capable of a torsional vibration parallel to the contact surface, and at least a first transducer cooperating with the resonator.

It is frequently desired to adjust the temperature of the reaction mixture to a defined value, either to achieve defined measurement conditions, or to induce reactions at elevated temperatures. For this purpose, the viscometer preferably includes a temperature-control element disposed near the contact surface. This may be a pure heating element, e.g. a heating wire, but is preferably an element which enables both heating and cooling, e.g. a Peltier element. The temperature-control element is preferably attached to the resonator. It can be produced by vapor deposition of metal layers on the resonator, especially if the latter comprises a glass tube.

The temperature-control element can, as current-carrying element, simultaneously serve to exert a force or a torque on the resonator through the Lorentz force acting in an external magnetic field. In this function, the temperature-control element may be part of the (electromagnetic) transducer. Conversely, vibration of the resonator in an external magnetic field then leads to induced voltages, which can be used to detect the vibration, in the temperature-control element. In this case, the viscometer preferably includes means for generating a static magnetic field, in particular one or more permanent magnets, in the vicinity of the temperature-control element.

In an advantageous embodiment, the resonator comprises a (mineral) glass tube with an external diameter of 1 millimeter or less. The external diameter is preferably 0.5 millimeter or less. The internal diameter is preferably 0.8 millimeter or less, particularly preferably 0.4 millimeter or less. The wall thickness is preferably between 0.02 millimeter and 0.1 millimeter, particularly preferably about 0.05 millimeter. The glass tube preferably consists of quartz glass. A resonator with such a glass tube has a high sensitivity, inter alia because of the particular mechanical properties of glasses, especially of quartz glass, and because of the low specific mass compared with many metallic materials. In addition, glass is to a large extent chemically inert, thus preventing the resonator material being attacked or chemically altered by the reaction mixture. A glass tube is moreover particularly suitable for vapor deposition of metal regions, thus making it possible to produce a temperature-control element particularly cost-effectively. This is of particular interest if the resonator is designed as a disposable product.

The glass tube is preferably fastened to a first and a second inertial mass whose mass is in each case a multiple (at least ten times) of the mass of the glass tube. Each inertial mass is connected directly or indirectly, e.g. via a weakened region, which acts as spring element, to a housing or holder. For further considerations concerning the inertial mass and connection thereof to the housing or holder, express reference is made to the disclosure in U.S. Pat. No. 4,920,787 and WO 95/24630. The transducer is disposed in the region between the inertial masses close to a vibration antinode (region of maximum amplitude) of a natural vibration of the resonator. The transducer is preferably located in the middle between the inertial masses. The interior of the tube forms the contact surface for the reaction mixture.

The glass tube is preferably detachably fastened to the inertial masses, e.g. by means of a clamp bush. The resonator is thus easily exchangeable, thus enabling it to be easily replaced after each measurement for hygiene reasons. In this case, it is particularly advantageous for current-carrying elements which are part of the transducer and serve to generate a magnetic field to be present on the glass tube.

In a further advantageous development, the resonator has a tube and a contact body. The latter is connected to the tube and has a diameter which is greater than the diameter of the tube, preferably at least twice the diameter of the glass tube. An external surface of the contact body forms the contact surface. The contact body is distinguished by being designed for a direct electromagnetic interaction with a magnetic field generated by the transducer, i.e. it is part of the (electromagnetic) transducer.

In a particular configuration, the contact body includes for this purpose a permanent magnet or is formed by such. The viscometer then comprises at least one pair of electromagnets which are disposed so that they interact magnetically with the permanent magnet. Alternatively, the contact body may also have at least one electromagnet.

In a further configuration, the apparatus includes a dosing device for the reaction mixture, which can be attached to a holder or housing or be formed by the housing itself. The dosing device is disposed close to the contact body and has an orifice in the region of the contact surface. The reaction mixture is introduced through this orifice into a predetermined region between the contact surface and the dosing device. The distance of the dosing device from the contact surface is such that the reaction mixture is kept by capillary forces in this predetermined region. The reaction mixture is thus confined in a defined sample volume.

In this configuration, the resonator preferably also includes a tube with, attached thereto, a contact body of larger diameter. In this case, the orifice is preferably disposed centrally, i.e. substantially concentrically with the tube.

The viscometer is preferably operated with a phase control loop as described in detail in U.S. Pat. No. 4,920,787 or WO 95/24630. For this purpose, the apparatus has a feedback unit which comprises an oscillator driving the first transducer. The feedback unit is intended to stabilize the resonator in the region of a characteristic frequency. For this purpose, an output terminal of the feedback unit is connected at least indirectly to the first transducer which stimulates the resonator to vibrations. The same transducer serves likewise to detect the vibrations, or a second transducer is present for this purpose on the resonator. An input terminal of the feedback device is connected at least indirectly to the first transducer or the second transducer. Operation with such a control loop makes particularly stable, reproducible measurements possible.

In order to make operation possible as disclosed in WO 95/24630, a first switch is present between the output terminal of the feedback device and the first transducer, and a second switch is present between the first or second transducer and the input terminal of the feedback device. The switches may include any suitable electronic means, e.g. transistors. The measurement can then take place in a gated mode without impairing the high frequency stability of the phase control loop.

In an apparatus configured in this way, the step of determining the measure of the viscosity preferably includes the following substeps:

stimulation of the first transducer with a signal generated by the feedback unit for a first pre-determined time interval, with, at least during this first time interval, the connection between the input terminal of the feedback device and the first or second transducer being interrupted;

feeding a signal generated by the first or second transducer to the feedback unit during a second pre-determined time interval, with, at least during this second time interval, the connection between the output terminal of the feedback device and the first transducer being interrupted.

This mode of operation has proved to be particularly robust, making it suitable in particular for small sample quantities.

The specific developments mentioned for a dynamic viscometer are, of course, also suitable for other purposes than determining the reaction status of a chemical reaction and display similar advantages therein.

BRIEF DESCRIPTION OF THE DRAWINGS

The invention is described in more detail below with reference to the drawings, which show.

DETAILED DESCRIPTION OF PREFERRED EMBODIMENTS

Figure 1:
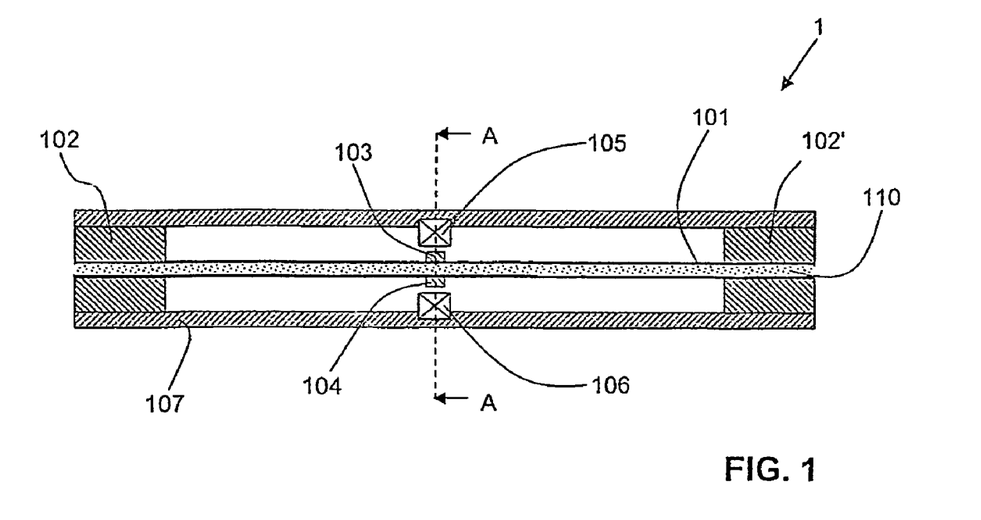
FIG. 1 a diagrammatic representation of a first embodiment of a viscometer of the invention viewed in section from above.
Figure 2:
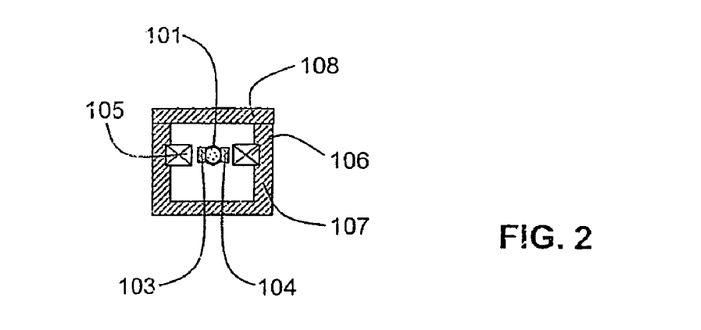
FIG. 2 a diagrammatic representation of the viscometer of FIG. 1 in cross section through plane A-A.

FIG. 1 shows in highly diagrammatic representation a first embodiment of an apparatus 1 according to the present invention. FIG. 2 shows the apparatus of FIG. 1 likewise highly diagrammatically in cross section seen in the direction A-A. Identical parts are provided with identical reference numbers.

A quartz glass tube 101 which forms the resonator is fastened in the region of each of its two ends to an inertial mass 102, 102'. The inertial masses are connected to a housing 107, e.g. by bonding. Both ends of the glass tube are accessible from the outside in order to introduce a liquid reaction mixture 110 into the glass tube. For this purpose, a certain region at both ends of the glass tube projects for example in a nondepicted manner out of the inertial masses, and suitable connections for feeding in the reaction mixture are provided. This is depicted for example in FIG. 12 of WO 95/24630. Thus, in operation, the interior of the glass tube serves as contact surface.

Two permanent magnets 103, 104 are bonded diametrically opposite on the middle of the tube 101. Two electromagnets 105, 106 are fastened in the housing 107 adjacent to the permanent magnets. The electromagnets 105, 106 form together with the permanent magnets 103, 104 an electromagnetic transducer for stimulating torsional vibrations of the tube 101 and for detecting such vibrations. The mode of functioning of such electromagnetic transducers is well known. In particular, the roles of permanent magnets and electromagnets may be exchanged. For the mode of functioning and configuration of such transducers, express reference is made to WO 95/24630, page 10, line 1 to page 11, line 9. A torque is exerted on the permanent magnets 103, 104 and thus on the central region of the tube by a current flowing in the electromagnets 105, 106 via magnetic forces. Conversely, a torsional movement of the tube induces a voltage in the electromagnets 105, 106, which can serve to detect torsional vibrations. The transducer thus serves alternately both as actuator for stimulation and as sensor for detection. It is, of course, also possible to provide separate transducers for these purposes.

FIGS. 1 and 2 are to be understood merely as diagrammatic representations. Thus, in particular, the diameter of the glass tube 101 is depicted greatly enlarged for reasons of depictability. In fact, the preferred external diameter of the glass tube is less than 1 millimeter, and is only 0.5 millimeter in a specifically implemented example. The wall thickness of the glass tube is preferably less than 0.1 millimeter, and is only 0.05 millimeter in said example. Thus, the internal diameter in said example is 0.4 millimeter. The length of the glass tube is preferably between about 30 millimeters and 100 millimeters, and is about 80 millimeters in said example. In this example, the volume of the sample chamber present in the interior of the glass tube is about 10 $mm^3$, that is 10 microliters. In such a viscometer, therefore, very small amounts of reaction mixture can be investigated.

The material of the glass tube is preferably a quartz glass. This material is preferred because it exhibits a very small internal damping and low density, thus making a high Q factor and a high sensitivity possible. Owing to the low modulus of rigidity of the material it is possible to prevent the boundary layer becoming too small. The resonance frequency of the fundamental vibration is preferably in the range between about 1 kHz and about 100 kHz; in said specifically implemented example it was about 14.7 kHz. The glass tube in this example was a commercially available quartz glass tube as is obtainable for example from VitroCom Inc., Mount Lakes, N.J. (USA).

The damping of the resonator is increased through the reaction mixture being in contact with the contact surface. The viscosity is determined from the measured damping of the resonator. This can take place analytically from the relation between viscosity and damping or through a calibration.

The apparatus is preferably operated as described in WO 95/24630. For this purpose, the electromagnets 105, 106 of the electromagnetic transducer are connected to a circuit as set forth in FIG. 1 to 8 and on page 4, line 1 to page 9, line 31 of WO 95/24630. Express reference is made to this disclosure for the design of the circuit for operating the apparatus and for the method of operation. The circuit is an example of a feedback circuit in order to stabilize the resonator close to its characteristic frequency. The damping of the resonator is determined by measuring the frequency shift on altering the phase between stimulating signal in the transducer and detected signal in the transducer.

The embodiment of FIGS. 1 and 2 is preferably configured so that all parts coming into contact with the reaction mixture, especially the glass tube 101, can easily be exchanged. For this purpose, the glass tube 101 is held in the inertial masses 102, 102' preferably with fastening means which are not depicted in detail and which permit the connection between glass tube and inertial mass to be broken easily. Suitable examples are clamp bushes made of plastic or metal as are well known in the art and which effect a secure connection between glass tube and inertial mass for example by screw tightening. It is important in this case that the connection is sufficiently firm for the glass region held in the fastening means in fact not to be capable of torsional vibrations.

Figure 3:
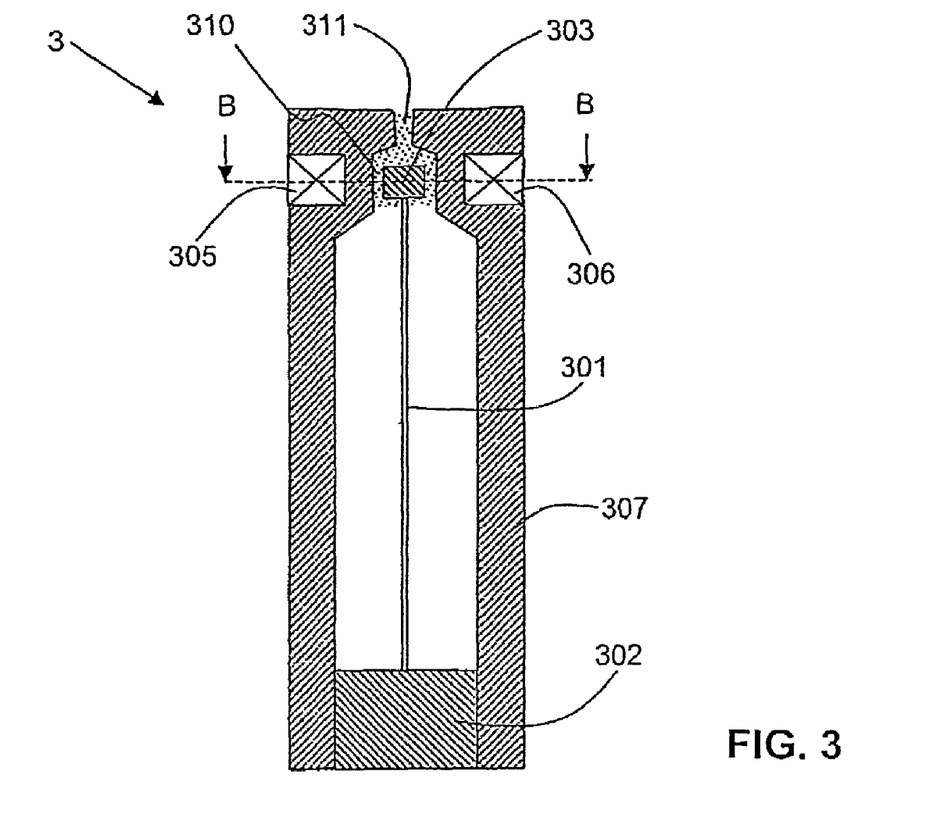
FIG. 3 a diagrammatic representation of a second embodiment of a viscometer of the invention viewed in section from the side.
Figure 4:
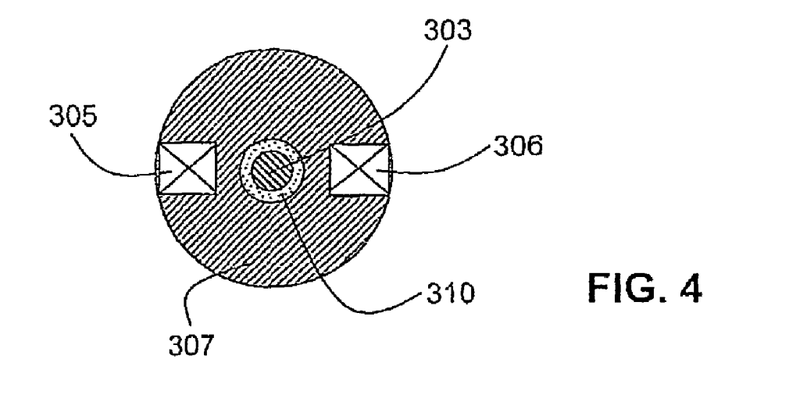
FIG. 4 a diagrammatic representation of the viscometer of FIG. 3 in cross section through plane B-B.

FIG. 3 shows a diagrammatic representation of a second embodiment of an apparatus of the invention, identified by the number 3. FIG. 4 shows the apparatus of FIG. 3 in cross section looking in the direction B-B. The resonator again includes a quartz glass tube 301 which is fastened by one end in an inertial mass 302. A cylindrical contact body 303 is placed on the other end. The inertial mass 302 is fastened in a housing 307. The latter is designed in the vicinity of the contact body to be so cylindrical that it encircles at a constant distance the contact body along its periphery. Opposite the front surface of the contact body there is an orifice 311 in the housing, through which a reaction mixture 310 can be introduced into the region limited by the contact body 303 and the housing 307. Beneath the contact body, the interior of the housing widens greatly. The orifice 311 likewise widens away from the contact body 303. These widenings, and the distances between contact body 303 and housing 307 are chosen so that the reaction mixture is held in the intended region by capillary forces. It is additionally possible, by suitable choice of the size of the contact body and of the distances, to reduce the quantity of the reaction mixture very greatly.

In the depicted embodiment, the contact body 303 is in the form of a permanent magnet whose magnetic field runs substantially perpendicular to the long axis of the tube 301. To prevent corrosion by the reaction mixture, the magnet can be provided with a chemically inert coating. This permanent magnet is suitable for magnetic interactions with two electromagnets 305, 306. Contact body 303 and electromagnets 305,

306 accordingly together form an electromagnetic transducer, and the contact body is itself part of this transducer.

In a specific embodiment, the contact body is formed for example by an Sm—Co permanent magnet which has been hydrophilicized on its surface by known methods in order to ensure good wetting.

Stimulation of the transducer with electrical signals of appropriate frequency stimulates the tube 301 to torsional vibrations, preferably in the fundamental vibration. The vibrations are detected by the same transducer as a sensor. The viscometer of FIG. 3 is operated in substantially the same way as that in FIG. 1; the statements made above concerning this accordingly apply analogously. The resonance frequency of the resonator is once again preferably in the range between 1 and 100 kHz.

FIGS. 3 and 4 are once again to be understood only as diagrammatic representations in which, in particular, the size relationships need not correspond to reality.

The statements made about FIGS. 1 and 2 apply in relation to the considerations of the dimensions of the glass tube. The distance between the contact body and the housing is to be chosen to be at least greater than the thickness of the boundary layer, formed during torsional vibration of the resonator, of the reaction mixture. Concerning further dimensions, the skilled worker is aware how these are to be chosen in order to achieve sufficient capillary forces depending on the material of the contact body and of the housing, and the composition of the reaction mixture. In a specific configuration, for example, the contact body has a diameter of 2.0 millimeters and a length of 0.7 millimeter. The internal diameter of the housing surrounding the contact body is 3.0 millimeters, i.e. the gap between contact body 303 and housing 307 has a width of 0.5 millimeter. The total sample volume in such a viscometer is about 15 microliters. It is of course possible for these dimensions to vary within a wide range depending on the specific area of use of the viscometer. One important aspect in the choice of the dimensions of the contact body is the resonance frequency of the resonator, which decreases as the mass of the contact body 303 increases.

The viscometer of FIG. 3 is suitable because of its simple design in particular also as a disposable viscometer whose parts which come into contact with the reaction mixture can simply be thrown away after use. In such a case, the electromagnets 305, 306 of the transducer are fastened to the housing 307 in an easily removable manner. Housing 307, inertial mass 302, tube 301 and contact body 303 form a disposable unit which can be thrown away after use and replaced by a new unit. The electromagnets 305, 306 and the drive electronics, which are not depicted, are by contrast reused. The housing can in such a case be manufactured cost-effectively from a synthetic material, e.g. polypropylene, in particular in a (precision) injection molding process. The same applies to the inertial mass. The electromagnets may also be held in a separate housing, e.g. a retaining ring, in which case the viscometer housing 307 is for example insertable therein.

Figures 5, 6, 7:
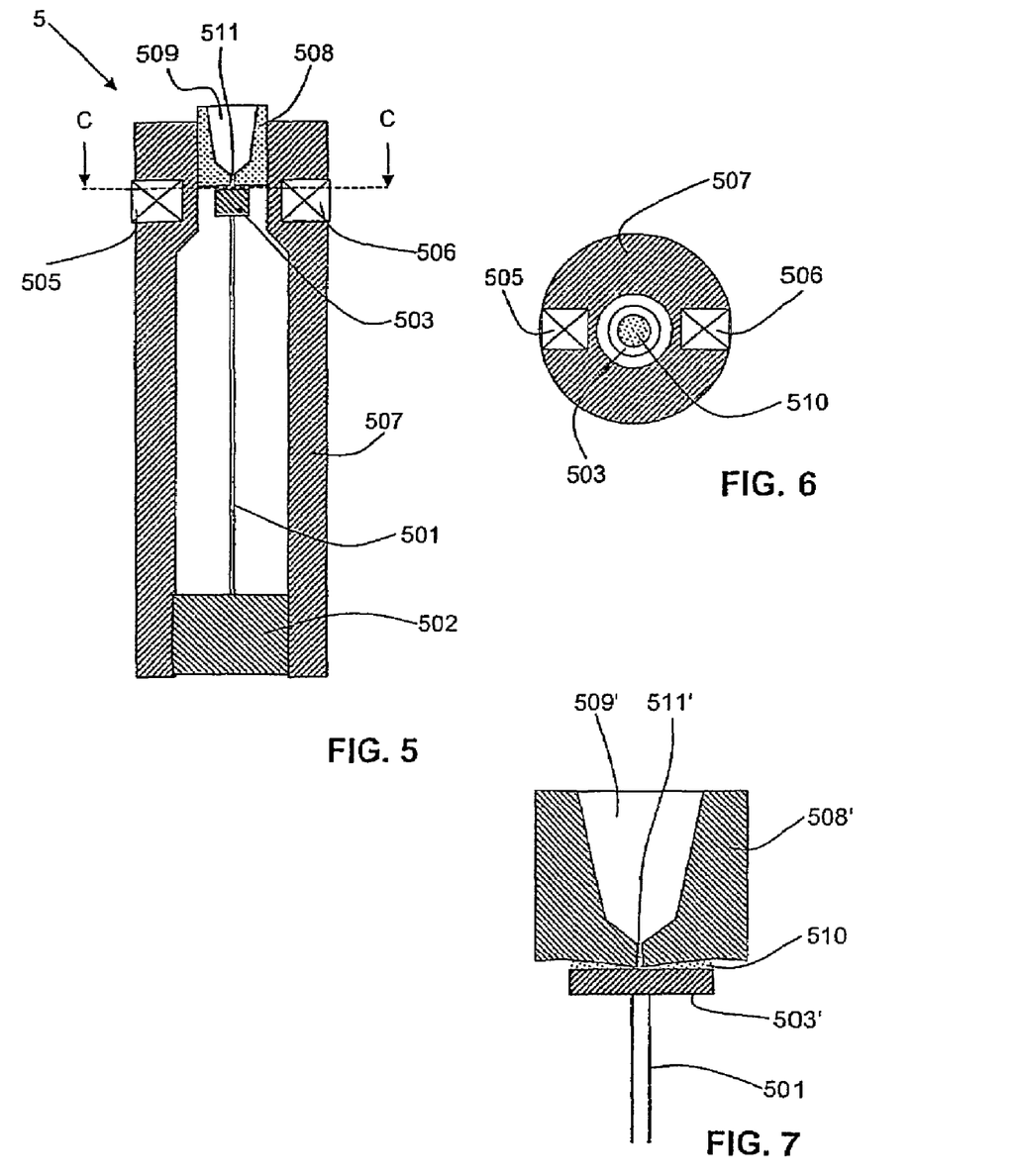
FIG. 5 a diagrammatic representation of a third embodiment of a viscometer of the invention viewed in section from the side.
FIG. 6 a diagrammatic representation of the viscometer of FIG. 3 in cross section through plane C-C.
FIG. 7 a diagrammatic enlarged partial representation of a variant of the third embodiment viewed in section from the side.

FIG. 5 shows a diagrammatic representation of a third embodiment of the apparatus of the invention identified by number 5. This apparatus is depicted in FIG. 6 in cross section looking in the direction C-C. Once again, the resonator includes a glass tube 501 which is connected at one end to an inertial mass 502. The inertial mass is inserted into a housing 507. A contact body 503 is once again attached at the other end of the glass tube 501. Just as in FIG. 3, this body is designed as a permanent magnet and interacts magnetically with electromagnets 505, 506. It is thus part of an electromagnetic transducer.

Opposite the front surface of the contact body 503, a dosing element 508 is screwed into the housing 507. This has a funnel-shaped dosing zone 509, which opens at the bottom into an orifice 511, to receive a reaction mixture 510. The reaction mixture passes through this orifice to the contact surface which is formed by the front surface of the contact body 503. The reaction mixture is held on this surface by capillary forces. The sample chamber is thus confined to the region between the front surface of the contact body 503 and the dosing element 508. The distance between contact body and dosing element can be varied for example by means of a fine thread, which is not depicted, on the cylindrical periphery of the dosing element 508, which cooperates with a corresponding internal thread of the housing 507. It is thus possible to restrict a reaction mixture to a thin layer whose thickness can be adjusted to the order of magnitude of the boundary layer which forms when the resonator executes torsional vibrations.

FIG. 7 shows a section of a similar viscometer which is constructed according to the principles of FIG. 5. Only part of the glass tube 501, the contact body 503' and the dosing element 508' with dosing zone 509' and orifice 511' are depicted, together with the reaction mixture 510. Whereas the front surface of the contact body 503' is flat, the dosing element 508' has a conical shape in the region opposite the front surface. There is a radial widening of the distance between the contact body 503' and the dosing element 508'. This configuration firstly ensures an effective restriction of the reaction mixture by capillary forces to the desired region. Secondly, this configuration ensures that a substantially spatially uniform shear rate (uniform rate gradient along the axial direction) is achieved over the whole reaction mixture. It is possible with this configuration to achieve very small sample volumes, in particular in the region of a few microliters.

The statements made about FIGS. 3 and 4 once again applies to the operation of an apparatus shown in FIG. 5 to 7.

Figure 8:
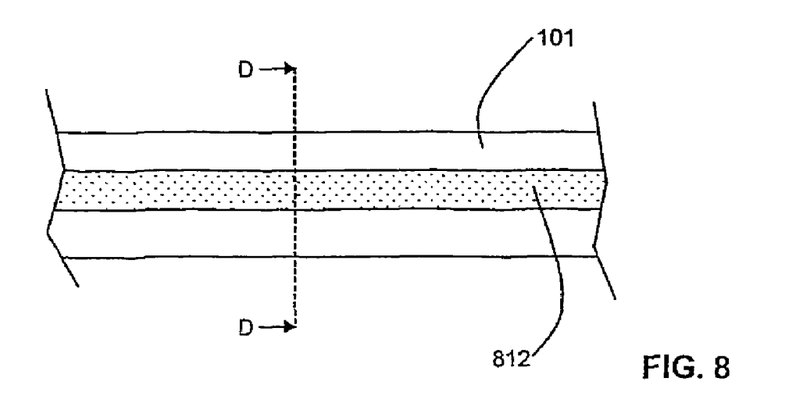
FIG. 8 a diagrammatic side view of a resonator tube.
Figure 9:
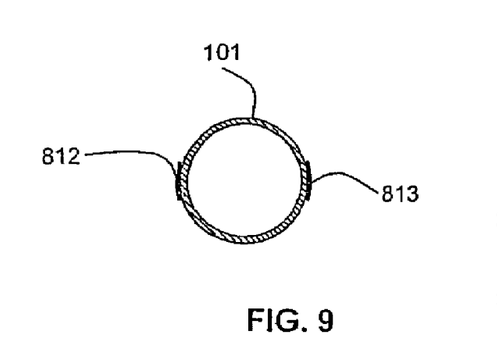
FIG. 9 a diagrammatic representation of the resonator tube of FIG. 8 in cross section through plane D-D.

The viscometers of the present invention can be provided with units for temperature control (heating and/or cooling) of the reaction mixture. FIG. 8 shows as example, diagrammatically and greatly enlarged, a part of a glass tube 101 of a viscometer as shown in FIG. 1. FIG. 9 depicts the glass tube in cross section looking in the direction D-D. Two metal strips 812, 813 are vapor-deposited on the glass tube 101 and act as heating wires. The reaction mixture present inside the glass tube 101 can easily be heated therewith. Instead of a layer running in the axial direction, it may also for example be coiled around the glass tube.

It is possible, alternatively or additionally, for a Peltier element as is well known to be disposed in the vicinity of the sample chamber. This makes it possible for the reaction mixture to be optionally heated or cooled. A suitable Peltier element can for example be applied (e.g. bonded) directly to the glass tube, or it can be formed on the glass tube by vapor deposition of two different metals. Depending on the direction of the current, a Peltier element can serve both as heating element and as cooling element.

In a preferred embodiment, the temperature-control element is simultaneously part of the electromagnetic transducer, i.e. a Lorentz force acts on the electrons in the metal of the temperature-control element in a magnetic field and is used to stimulate the resonator and/or to detect the vibrations of the resonator. For this purpose, in addition to the temperature-control element, further metal strips may also be vapor-deposited or applied in another way, e.g. in the form of coils. The temperature-control element acting as part of the transducer, and/or the additional metal strips, may be operated with direct current in a first operating mode. In operation, they then cooperate with an alternating magnetic field which is generated by the electromagnets 105, 106 in order to stimulate the resonator. Alternatively, they may also be operated with alternating current. In this case, the coils 105, 106 can be replaced by permanent magnets, and both the stimulation and the vibration detection takes place completely by means of the temperature-control element and/or of the additional metal strips, instead by means of the coils 105, 106.

Especially when a Peltier element is part of the transducer it is advantageously operated with alternating current for the purposes of stimulation, so that a negligible cooling or heating effect takes place, because cooling effect and heating effect are substantially canceled over a period of the alternating current.

The metal regions present on the glass tube 101 can be connected in a known manner to electrical supply lines. For this purpose, for example, contact zones are formed near the ends of the glass tube. After the glass tube has been inserted into the inertial masses, these contact zones are in contact with contacts for the electrical supply lines which are provided for example in the borehole of the inertial masses or at another suitable point.

Such a configuration is advantageous especially when the glass tube is configured as a disposable glass tube, i.e. is designed to be removed and replaced after use. It is possible in particular to dispense with the permanent magnets 103, 104, leading to a marked saving in costs.

Figure 10:
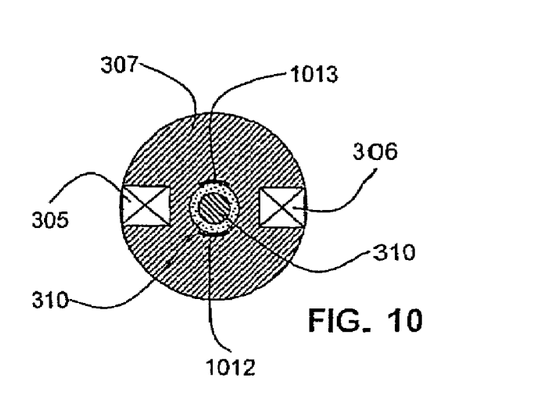
FIG. 10 a diagrammatic representation of a variant of the third embodiment of a viscometer of the invention in cross section.

As a further example, FIG. 10 shows a variant of the viscometer of FIG. 4, in which two heating elements 1012, 1013 are present on the inner surface of the housing 307 which surrounds the contact body 303. These may be formed for example from current-carrying pieces of wire or be formed in another known manner.

It is also possible for a plurality of temperature-control elements to be present, making it possible for example to generate temperature gradients. Suitable temperature sensors as are well known in the art (e.g. Pt-100 sensors etc.) are also preferably present.

The presence of one or more temperature-control elements is particularly beneficial especially when a reaction is to be carried out directly in the viscometer, but also has other advantages because the viscosity is usually highly temperature-dependent and a control of the temperature may improve the reproducibility of the measurement. Thus, if a cooling element is present, the reaction mixture can for example be cooled to a temperature close to the solidification point of the reaction mixture, e.g. into the range between 0° C. and 10° C. for dilute aqueous solutions, usually bringing about a significant increase in viscosity, and be stabilized there. Stabilization in a range of, for example ±0.1° C. will often be necessary and can be achieved more quickly and easily with said temperature-control elements than with temperature control of the entire viscometer.

A temperature control is of particular interest when a reaction for amplifying nucleic acid fragments is carried out, especially a PCR or LCR, which often require temperature alterations (temperature cycles). It is possible through the temperature control for the reaction to take place directly in the sample chamber of the viscometer, and the amplification can be followed directly at suitable points in the temperature cycles by means of the change in viscosity. In a method for detecting mutations by means of allele-specific amplification, the reaction can for example be terminated immediately when a change in viscosity indicating the presence of the mutation occurs. If the temperature of the viscometer is not controlled, the amplification is carried out in a separate reaction apparatus for the amplification process initially for a fixed number of cycles. The sample must then be removed from the reaction apparatus and only then transferred into the viscometer. It is obvious that this involves greater expenditure of time and effort.

The use of the method of the invention in a reaction for amplifying nucleic acids is now to be explained by way of example for use for detecting mutations.

Use: Detecting Mutations

Various methods are now normally used to detect mutations of nucleic acids (DNA and RNA). Mutations of the genetic material include the absence of single base pairs (single nucleotide polymorphisms SNPs), the absence of a whole sequence unit (deletion) or the presence of surplus genetic information (insertion). Examples which may be mentioned of the detection of such alterations in genetic material are gel electrophoresis with restriction enzymes, which uses ethidium bromide as staining method. A more modern example is real-time PCR with fluorophores to visualize the reaction. These processes are costly, time-consuming and relatively expensive.

The method of the invention represents a cost-effective alternative with which it is possible to determine a mutation in the genetic material. The method advantageously takes place in the following phases:

isolation of the nucleic acids;

amplification of the sequence to be investigated, e.g. by means of a polymerase chain reaction (PCR);

linkage of the fragments produced in the amplification reaction by means of a ligase chain reaction (LCR) with probe molecules (allele-specific) specifically designed as linkers;

determining the viscosity of the reaction product.

The increase in viscosity in a chemical process such as PCR can in principle be calculated theoretically. In this case, nucleotides are converted into longer, double-stranded products, so that the molecules become larger and water, which previously surrounded the nucleotides, is released. The viscosity will change during this, because polymers are synthesized. The so-called templates produced in the reaction frequently achieve a size of 250 to 500 mer.

However, the amplification process is frequently insufficient on its own for a significant increase in viscosity to be measurable. For this reason, the molecules produced in the amplification are preferably connected together (linear linkage and/or crosslinking). This process is carried out subsequent to the amplification or coupled therewith. The linkage is in this case preferably carried out using an LCR with incorporation of suitable linker molecules.

EXAMPLE

Detection of the "Factor V Leiden" Mutation

The factor V Leiden mutation is a single point mutation (G instead of A) in the human gene sequence, leading to a glutamine residue being replaced by an arginine residue at position 506 in the protein (a clotting factor) encoded by the sequence. Further information on this mutation is to be found for example in R. M. Bertina et al., "Mutation in Blood Coagulation Factor V Associated with Resistance to Activated Protein C", Nature 369, 64-67 (1994). The entire nucleotide sequence of the factor V gene is described in: R. J. Jenny et al., "Complete cDNA and Derived Amino Acid Sequence of Human Factor V", Proc. Nat. Acad. USA 84, 4846-4850 (1987). The risk of thrombosis is markedly increased in individuals having the mutation compared with individuals of the wild type, which is, why this mutation is the subject of a laboratory test which is frequently carried out in clinical genetics laboratories.

In the method normally carried out to identify the mutation, the gene segment is amplified by PCR. The amplification product is digested with a restriction endonuclease which cuts only the wild-type sequence, but not the mutant. Wild type and mutant can then be differentiated by gel electrophoresis. This method is time-consuming and requires a large number of manual steps.

An alternative proposal in U.S. Pat. No. 6,174,670 is to monitor the PCR process by means of fluorescence. Although this method is substantially faster it is relatively expensive because of the need for optical components and the use of fluorescence markers.

It is therefore demonstrated hereinafter that mutation of the Leiden V gene can also be examined very cost-effectively, simply and quickly using dynamic viscometry.

Hereinafter, "mutation site" refers to that nucleotide position in the factor V gene where a guanine base in the wild type is replaced by an adenine base in the mutant.

Figure 11:
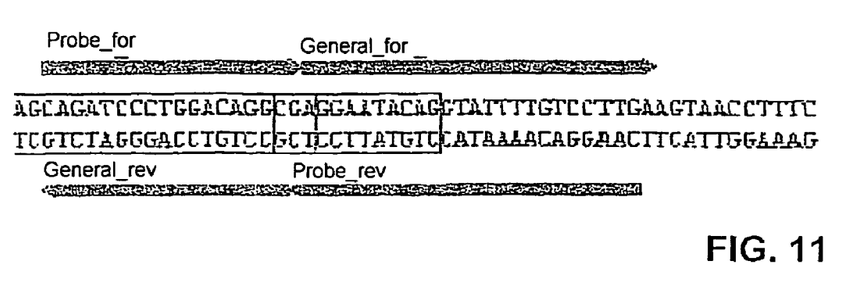
FIG. 11 a diagram to illustrate the position of various nucleotide sequences.

The DNA oligonucleotides indicated in Table 1 were synthesized beforehand (TIB-MOLBIOL, Berlin). FIG. 11 illustrates in this connection how these oligonucleotides correspond to the sequence of the factor V gene. A segment of the double strand of the factor V gene in the vicinity of the mutation site is depicted in the middle of FIG. 11. The oligonucleotides are designed to hybridize onto the indicated sites on the single strands. In this connection, "probe_for" stands for either "wild type_for" or "mutation_for", and corresponding "probe_rev" stands for either "wild type_rev" or "mutation_rev". In a "normal" LCR, the oligonucleotide "probe_for" serves for connection to the oligonucleotide "general_for" which is phosphorylated at the 5' end, and analogously the oligonuleotide "probe_rev" serves for connection to the 5'-phosphorylated oligonucleotide "general_rev". The molecules "WT_Linker_for", "WT_Linker_rev", "Mut_Linker_for" and "Mut_Linker_rev" are produced by connecting these molecules via a linker of (preferably) nine T bases and are designed to hybridize with their segments on the 5' side to a first nucleotide and Zenith their segments on the 3' side to another nucleotide.

The letter "p" therein indicates that the respective base is phosphorylated at the relevant 5' or 3' end. Tm indicates the melting point calculated by the nearest neighbor method. These oligonucleotides served as primers or probes for the reactions described hereinafter.

The investigation for the presence of the mutation comprised provision of a sample of human DNA which comprised the mutation site, amplification by means of PCR, followed by a "normal" LCR or an allele-specific and specifically adapted LCR, finally followed by a viscosity measurement.

Human genomic DNA (initial DNA) was isolated from whole blood by methods like those well known in the art, see, for example, J. Sambrook et al., "Molecular Cloning: A Laboratory Manual" (2nd edition, 1989), Chapter 9.

The nucleic acid isolate was used initially to carry out a PCR for (non-specific) amplification of the initial DNA as follows: the primers used were the abovementioned oligonucleotides "Primer_for" (SEQ ID NO 1) and "Primer_rev" (SEQ ID NO 2). A PCR was carried out in accordance with the following protocol:

Denaturation: 95° C., 1 s
Annealing: 55° C., 10 s
Elongation: 72° C., 15 s
Cycles: 20
Concentrations: 0.5 micromole of each oligonucleotide
Taq polymerase 5 U/microliter, in total 3 microliters
$MgCl_2$: 3 mM
dNTPs: 50 micromole The PCR was only optionally followed by a "normal" LCR. The LCR was carried out as follows: "Ampligase 1× Reaction Buffer" from Epicentre Technologies (20 mM Tris-HCl (pH 8.3), 25 mM KCl, 10 mM $MgCl_2$, 0.5 mM NAD, and 0.01% Triton X-100) was provided. The following were added to 50 microliters of reaction buffer: 50 nmol of each of said probes "Probe_for" (SEQ ID NO 3 or 4), "General_for" (SEQ ID NO 5), "Probe_rev" (SEQ ID NO 6 or 7) and "General_rev" (SEQ ID NO 8), 1.5-5 U of Ampligase (Epicentre Technologies). The Ampligase concentration depends

TABLE 1

DNA oligonucleotides for analyzing the factor V Leiden mutation.

| Name | Sequence (5'→3') | ID | Tm |
|---|---|---|---|
| Primer_for | TAATCTGTAA GAGCAGATCC | SEQ ID NO: 1 | |
| Primer_rev | TGTTATCACA CTGGTGCTAA | SEQ ID NO: 2 | |
| Wild type_for | AGATCCCTGG ACAGGCG | SEQ ID NO: 3 | 56.1° C. |
| Mutation_for | CAGATCCCTG GACAGGCA | SEQ ID NO: 4 | 56.4° C. |
| General_for | p-AGGAATACAG GTATTTTGTC CTTGA | SEQ ID NO: 5 | 55.6° C. |
| Wild type_rev | CAAGGACAAA ATACCTGTAT TCCTC | SEQ ID NO: 6 | 55.6° C. |
| Mutation_rev | CAAGGACAAA ATACCTGTAT TCCTT | SEQ ID NO: 7 | 55.7° C. |
| General_rev | p-GCCTGTCCAG GGATCTG | SEQ ID NO: 8 | 53.6° C. |
| WT_Linker_for | p-AGGAATACAG GTATTTTGTC CTTGATTTTT TTTTAGATCC CTGGACAGGC G | SEQ ID NO: 9 | |
| WT_Linker_rev | p-GCCTGTCCAG GGATCTGTTT TTTTTTCAAG GACAAAATAC CTGTATTCCT C | SEQ ID NO: 10 | |
| Mut_Linker_for | p-AGGAATACAG GTATTTTGTC CTTGATTTTT TTTTAGATCC CTGGACAGGC A | SEQ ID NO: 11 | |
| Mut_Linker_rev | p-GCCTGTCCAG GGATCTGTTT TTTTTTCAAG GACAAAATAC CTGTATTCCT T | SEQ ID NO: 12 | | on the type of Ampligase employed. 30 seconds' incubation at 95° C., followed by 30 seconds, incubation at 50° C. for 45 seconds; 35 cycles.

In this case, a normal allele-specific LCR takes place in which the ligase links in each case to forward or reverse probes which are hybridized onto the same nucleotide. The resulting nucleotides thus undergo no further linkage (interlinkage or crosslinking).

Alternatively, a specifically adapted LCR was carried out. The LCR in this case was configured so that crosslinking of the resulting nucleic acid fragments takes place simultaneously. For this purpose, the probes "WT_Linker_for" (SEQ ID NO 9) and "WT_Linker_rev" (SEQ ID NO 10) served as specific bridging molecules which bind between the two ends of each one of the PCR products synthesized by the polymerase. Thus, for example, the probe "WT_Linker_for" (SEQ ID NO 9) includes both the sequence of the probe "General_for" (SEQ ID NO 5) and the sequence "Wild type_for" (SEQ ID NO 3). These are connected by means of a linker region of 9 T bases, it also being possible to choose a different number of bases. Between 5 and 20 bases in the linker region appear to be reasonable, preferably 5 to 10.

During the LCR, the 5' region of the probe "WT_Linker_for" (SEQ ID NO 8) now hybridizes onto the corresponding region of a first nucleotide, while the 3' region hybridizes onto the corresponding region of a second nucleotide. If the 5' end of a further probe molecule is hybridized onto this second nucleotide, the two probe molecules are connected by the ligase. A longer-chain polymer is produced in this way. The production of this polymer leads to a marked rise in viscosity.

However, the ligase linkage will take place only if the sequence of the probe at the 3' end corresponds exactly to the sequence of the nucleotide. A single base exchange at the 3' end will therefore inhibit the LCR. The LCR is additionally allele-specific in this way.

The above explanation related to the probe "WT_Linker_for", but applies analogously also to the probe "WT_Linker_rev". The reaction is carried out simultaneously on the (+) and (−) DNA strand, in the presence of both probes.

Thus, overall, the LCR is allele-specific and leads simultaneously to polymerization of probe molecules.

The adapted LCR was carried out as follows: "Ampligase 1× Reaction Buffer" from Epicentre Technologies: 50 microliters of reaction buffer, 50 nmol each of said probes "WT_Linker_for", "WT_Linker_rev", 1.5-5 U of Ampligase (Epicentre Technologies). The Ampligase concentration depends on the type of Ampligase employed. 30 seconds' incubation at 95° C., followed by 30 seconds' incubation at 50° C. for 45 seconds; 35 cycles.

The product was subsequently examined in a dynamic viscometer as depicted in FIG. 1 (quartz glass tube as resonator, length 80 mm, external diameter 0.5 mm, wall thickness 0.05 mm). In this case, the sample was cooled to 10° C. and the temperature was stabilized in a range of ±0.1° C.

The viscosity of the following samples was determined.

Reference Measurements:
Sample 1 $H_2O$ (PCR grade)
Sample 6 Buffer solution for PCR (no further additions)
Sample 7 Buffer solution for LCR (no further additions)

Neither a PCR nor an LCR was carried out on these samples.

Control Measurements:
Sample 9 LCR buffer to which a wt sample polymerized previously with linker molecules from a different system was added Sample 10 PCR buffer with the dye SYBR Green, to which a wt sample polymerized previously with linker molecules from a different system was added No further PCR or LCR was carried out on these samples either.

The further samples had the composition shown in Table 2. The meanings here are:

Target DNA Target DNA was present as follows: wt=wild type (healthy); mut=homozygous mutation.

PCR If yes: a PCR was carried out before the subsequent LCR.

LCR conv. If yes: a conventional LCR was carried out with probes of the indicated SEQ ID NO from Table 1, i.e. with probes without linker.

LCR linker If yes: an adapted LCR was carried out with the linker probes of the indicated SEQ ID NO from Table 1, i.e. an LCR with simultaneous polymerization of the probe molecules.

TABLE 2

Samples for viscosity measurements

| Number | Target DNA | PCR | LCR conv. (probes) | LCR linker (probes) |
|---|---|---|---|---|
| 1 | | | $H_2O$, PCR grade | |
| 2 | wt | no | yes (3, 5, 6, 8) | no |
| 3 | wt | no | yes (3, 5, 6, 8) | no |
| 4 | mut | yes | yes (3, 5, 6, 8) | no |
| 5 | wt | yes | yes (4, 5, 7, 8) | no |
| 6 | | | Buffer for PCR, no other additions | |
| 7 | | | Buffer for LCR, no other additions | |
| 8 | wt | yes | no | yes mut linker (11, 12) |
| 9 | | | LCR buffer with linked wt sample from a different system | |
| 10 | | | PCR buffer with SYBR Green, with linked wt sample from a different system | |
| 11 | mut | yes | no | yes mut linker (11, 12) |
| 12 | wt | no | no | yes, wt linker (9, 10) |
| 13 | mut | yes | no | yes, mut linker (11, 12) |
| 14 | mut | no | no | yes, mut linker (11, 12) |
| 15 | wt | yes | no | yes, wt linker (9, 10) |

Figure 12:
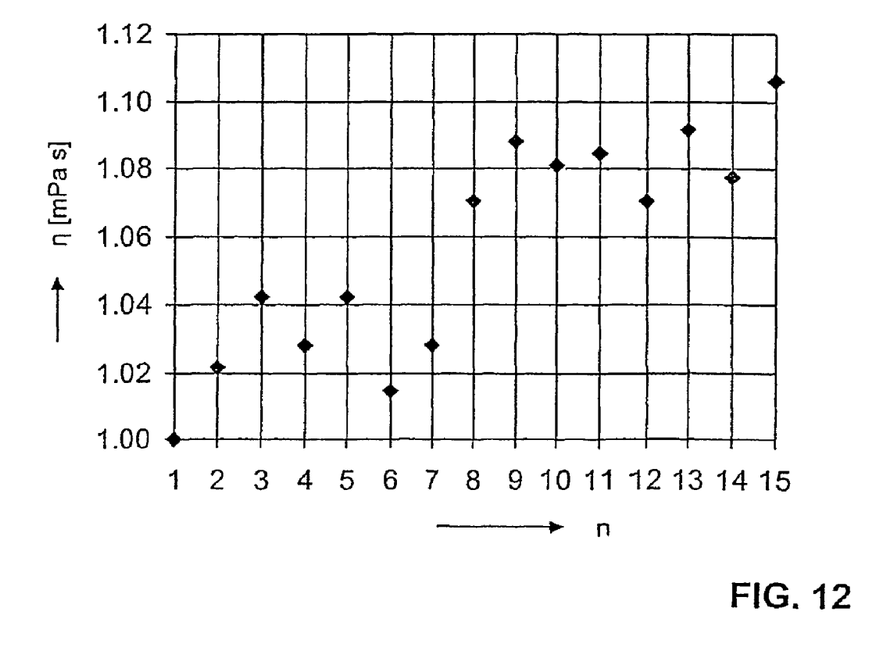
FIG. 12 a diagram with measurements of the viscosity for various samples.

The results are depicted in FIG. 12. This is a graphical representation of the result of viscosity measurements on the samples indicated in Table 2.

In this case, the symbol n designates the serial number of the measurement, η designates the viscosity. In addition, further control measurements which are not represented were also carried out.

The results showed that detection of a mutation is possible by dynamic viscometry. An increase in viscosity occurs only if the amplification has resulted in sufficient nucleic acid fragments as a product which can serve as templates in the subsequent adapted LCR. The presence or absence of the mutation can thus be concluded from the presence or absence of a change in viscosity in the ligase linkage.

It should be emphasized that the invention is by no means confined to the above examples. Thus, in particular, diverse change in the chemistry design are possible in the method for determining the reaction status of an amplification reaction.

Thus, the number of nucleic acids already present is crucial for the design of the method. If a sufficient number of molecules is present, it is possible for example to dispense with a PCR amplification and to carry out the LCR immediately. For example, to detect DNA from suspensions of bacteria it is possible, as an alternative to PCR with coupled LCR, also to carry out an LCR alone, without PCR. Similarly, to detect thymus DNA it is possible to carry out only a PCR or only an LCR if the amount of nucleic acid is so large that a change in viscosity is measurable by one of these methods alone.

Although the specifically adapted LCR as described herein is advantageous, it is not absolutely essential in all situations. Thus, in some circumstances, solely the increase in viscosity on the basis of a PCR or of a conventional LCR may suffice for detection. If the number of nucleic acid sequences is sufficiently high, it would in particular be possible solely by means of allele-specific amplification to detect an increase in product on the basis of an increase in viscosity, as a type of "real-time PCR".

In order to be able to detect a point mutation (SNP) by means of an increase in viscosity, the PCR process can also be made dependent on the mutation if the amplification takes place only if the mutation is present. In such a case, only the amplified sequences could then be ligated in the subsequent LCR, i.e. only those of a mutation. No PCR can be carried out on the unmutated ones, and accordingly there is also too little precursor for an LCR which, as a consequence, does not lead to an increase in viscosity either. Such a selective amplification is achieved by means of allele-specific amplification in which a primer is developed for the mutation. Such methods are well known in the art.

A method in which a PCR cycle and an LCR cycle or a so-called ligation detection reaction (LDR) is performed alternately is also conceivable.

A further possibility consists of carrying out a PCR followed by an oligonucleotide ligation assay (OLA) in which the ligation of two neighboring probes is utilized as single detection step.

However, all these methods will have a lower sensitivity than the combination of PCR with the abovementioned specifically adapted LCR, which leads to further interlinkage of the resulting oligonucleotides.

A further very interesting possibility consists of carrying out a gap LCR instead of the PCR or subsequent to the PCR. In a gap LCR, complementary probe pairs are employed with a 3' extension. After they have hybridized onto the target sequence DNA, there is a gap of one or more bases to the neighboring probe. The thermostable polymerase (for the automation process) without 3'→5' exonuclease activity, and the appropriate nucleotides (float in solution) are used to couple the gap and the resulting probes with DNA ligase. The use of probe duplexes with non-complementary 3' extensions prevents the formation of target molecule-independent ligase products (so-called blunt-end ligation). There are studies showing that fewer than 10 molecules per reaction mixture can be detected therewith.

In an alternative experiment, a gap LCR was carried out instead of the PCR. A reaction mixture was made up as follows. "Ampligase 10× Reaction Buffer" from Epicentre Technologies was used as reaction buffer. This contained: 200 mM Tris-HCl (pH 8.3), 250 mM KCl, 100 mM $MgCl_2$, 5 mM NAD and 0.1% Triton X-100. The following were added to 50 microliters of reaction buffer: 50 nmol each of suitable probes for the gap LCR, 1.5 U of DNA polymerase without 3'→5' exonuclease activity (from Thermus flavus) (MBR, Milwaukee, Wis.), 20 mM $K^+$, 1.5-5 U of Ampligase (Epicentre Technologies). The Ampligase concentration depends on the type of Ampligase employed. Definition of the unit U: one unit U catalyzes the ligation of 50% of the cos sites in 1 microgram of lambda-DNA in 1 minute at 45° C. in "1× Ampligase Reaction Buffer". 1 U of Ampligase DNA ligase is equivalent to at least 15 cohesive end units or nick ligation units as otherwise frequently used in the art. The Ampligase was provided in a storage buffer which had the following composition: 50% glycerol with 50 mM Tris-HCl (pH 7.5), 0.1 M NaCl, 0.1 mM EDTA, 1 mM DTT, and 0.1% Triton X-100. The reaction volume was covered with 50 microliters of mineral oil.

Further evaluation took place as in the above example. The result was comparable with that following a PCR.

An adapted gap LCR in which the probes are designed so that they hybridize with their ends on different nucleic acid fragments, analogous to the adapted LCR described above, is also conceivable.

The proposed methods result in a series of advantages compared with a conventional PCR with fluorescence detection. Of these, the following advantages should be particularly emphasized.

Detection is very cost-effective (up to a factor of 20 more effective than with optical detection).

No labeling (dye coupling) is necessary. The synthesis is therefore more cost effective.

No specific hybridization probes need to be developed.

The reaction can be pooled, i.e. it is possible to test 10, 50, 100 or even more patients simultaneously. If no increase in viscosity occurs, none of the tested samples has a mutation (if the design is for the mutation). If an increase in viscosity is recorded, one or more samples must be mutated. The mutation can be deduced by subsequently dividing the pool.

The reaction can be automated: either using a robot pipette or with thermostable ligase.

The reaction is multifaceted. There are some subvariants which make application highly interesting, such as, for example, the differentiation of microorganisms. Microorganisms having similar sequences can be differentiated only with difficulty by means of allele-specific amplification. However, such a selection would certainly be possible in a first process. In a following step, the product is then subjected to a sequence-specific crosslinking. This might take place for example with a selective tethering of the molecules in the reaction vessel (well). The coupling and tethering takes place with streptavidin/biotin. The capture probe (complementary) would be able to hybridize the corresponding fragments. In addition, branches which are developed for the sequence differences of the subspecies are now activated, e.g. by means of dendrimers which in turn form a network and thus the viscosity in the event of the presence of a particular sequence and thus species become active and increase the viscosity.

It is generally clear from the above that the method of the invention is generally suitable for determining the reaction status of an amplification reaction, but also for other viscosity-altering chemical reactions, especially when the sample quantities are small.

Diverse variations are also possible in the apparatus of the invention without leaving the scope of the invention, as is evident from the examples described above, and the invention is by no means restricted to these examples.

LIST OF REFERENCE NUMBERS

1 Viscometer (first embodiment)
101 Glass tube
102, 102' Inertial mass
103, 104 Permanent magnet
105, 106 Electromagnet
107 Housing
110 Reaction mixture A-A Plane of section
3 Viscometer (second embodiment)
301 Glass tube
302 Inertial mass
303 Contact body (permanent magnetic)
305, 306 Electromagnet
307 Housing
310 Reaction mixture
311 Orifice
B-B Plane of section
5 Viscometer (third embodiment)
501 Glass tube
502 Inertial mass
503, 503' Contact body (permanent magnetic)
505, 506 Electromagnet
507 Housing
508, 508' Dosing insert
509, 509' Dosing zone
510 Reaction mixture
511, 511' Orifice
C-C Plane of section
812, 813 Heating element
D-D Plane of section
1012, 1013 Heating element n Measurement number
η Viscosity
Sequence Listing—Free Text
SEQ ID NO 1 Primer for PCR, forward strand
SEQ ID NO 2 Primer for PCR, reverse strand
SEQ ID NO 3 Probe for LCR, wild type-specific, forward strand
SEQ ID NO 4 Probe for LCR, mutation-specific, forward strand
SEQ ID NO 5 Probe for LCR, nonspecific, 5' end phosphorylated, forward strand
SEQ ID NO 6 Probe for LCR, wild type-specific, reverse strand
SEQ ID NO 7 Probe for LCR, mutation-specific, reverse strand
SEQ ID NO 8 Probe for LCR, nonspecific, 5' end phosphorylated, reverse strand
SEQ ID NO 9 Linker probe for adapted LCR, wild type-specific, 5' end phosphorylated, forward strand
SEQ ID NO 10 Linker probe for adapted LCR, wild type-specific, 5' end phosphorylated, reverse strand
SEQ ID NO 11 Linker probe for adapted LCR, mutation-specific, 5' end phosphorylated, forward strand
SEQ ID NO 12 Linker probe for adapted LCR, mutation-specific, 5' end phosphorylated, reverse strand

The invention claimed is:

1. A method for determining the reaction status of a chemical reaction process in a reaction mixture, the method comprising:
   providing a dynamic viscometer comprising a resonator and at least a first transducer cooperating with the resonator, the resonator being capable of a mechanical natural vibration with a characteristic frequency and having a contact surface;
   contacting the reaction mixture with the contact surface; and
   carrying out a reaction process in the reaction mixture while the reaction mixture is in contact with the contact surface, the reaction process comprising amplifying nucleic acids, and
   determining the viscosity of the reaction mixture by means of the dynamic viscometer to determine the reaction status of the reaction process while the reaction mixture is in contact with the contact surface.

2. The method as claimed in claim 1, wherein the reaction process comprises at least one of a polymerase chain reaction and a ligase chain reaction.

3. The method as claimed in claim 1, wherein the reaction process comprises an allele-specific amplification reaction.

4. The method as claimed in claim 1, wherein the reaction process comprises a linkage of nucleic acid fragments by means of a linker oligonucleotide which is designed to hybridize with one region near its 5' end on a first nucleic acid fragment, and to hybridize with a region near its 3' end on a second nucleic acid fragment.

5. The method as claimed in claim 1, wherein the reaction mixture in contact with the contact surface is located in a sample chamber having a volume which is less than 1 milliliter.

6. The method as claimed in claim 1, wherein the reaction mixture is at least partly held by capillary forces in the sample chamber.

7. The method as claimed in claim 1, the method comprising gated operation of the dynamic viscometer.

8. The method as claimed in claim 1, wherein the dynamic viscometer comprises a tube.

9. The method as claimed in claim 1, the method comprising carrying out thermal cycles, wherein the tube is used both for the thermal cycles and for measuring the viscosity.

10. The method as claimed in claim 4, wherein the linkage of nucleic acid fragments results in a network.

11. The method as claimed in claim 10, wherein said network is formed after an amplification reaction has been carried out.

12. The method as claimed in claim 4, wherein the linker oligonucleotide comprises a linker region having a repetitive arrangement of identical bases.

13. The method as claimed in claim 4, wherein the linker oligonucleotide comprises a linker region having a repetitive arrangement of 5 to 20 identical bases.

14. The method as claimed in claim 4, wherein the linker oligonucleotide comprises a linker region having a repetitive arrangement of 5 to 20 T bases.

15. The method as claimed in claim 4, wherein the 5' end of the linker oligonucleotide is phosphorylated.

16. The method as claimed in claim 1, wherein temperature of the reaction mixture during the reaction process and during the determination of viscosity is controlled by a temperature-control element disposed near the contact surface.

17. The method as claimed in claim 16, wherein the temperature-control element is an element operative for both heating and cooling.

18. The method as claimed in claim 16, wherein the temperature-control element is a Peltier element.

19. The method as claimed in claim 16, wherein the temperature-control element is attached to the resonator.

20. The method as claimed in claim 16, wherein the temperature-control element comprises at least one vapor-deposited of metal layer on the resonator.

21. The method as claimed in claim 16, wherein the temperature-control element is part of the first transducer.

* * * * *

```
                             SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Primer for PCR, forward strand

<400> SEQUENCE: 1
taatctgtaa gagcagatcc                                                   20

<210> SEQ ID NO 2
<211> LENGTH: 20
<212> TYPE: DNA
<213> ORGANISM: Artificial Sequence
<220> FEATURE:
<223> OTHER INFORMATION: Primer for PCR, reverse strand

<400> SEQUENCE: 2
tgttatcaca ctggtgctaa                                                   20

<210> SEQ ID NO 3
<211> LENGTH: 17
<212> TYPE: DNA
<213> ORGANISM: Artificial Sequence
<220> FEATURE:
<223> OTHER INFORMATION: Probe for LCR, wildtype-specific, forward
      strand

<400> SEQUENCE: 3
agatccctgg acaggcg                                                      17

<210> SEQ ID NO 4
<211> LENGTH: 18
<212> TYPE: DNA
<213> ORGANISM: Artificial Sequence
```

```
<220> FEATURE:
<223> OTHER INFORMATION: Probe for LCR, mutation-specific, forward
      strand

<400> SEQUENCE: 4
cagatccctg gacaggca                                                      18

<210> SEQ ID NO 5
<211> LENGTH: 25
<212> TYPE: DNA
<213> ORGANISM: Artificial Sequence
<220> FEATURE:
<223> OTHER INFORMATION: Probe for LCR, unspecific, 5' end
      phosphorylated, forward strand

<400> SEQUENCE: 5
aggaatacag gtattttgtc cttga                                              25

<210> SEQ ID NO 6
<211> LENGTH: 25
<212> TYPE: DNA
<213> ORGANISM: Artificial Sequence
<220> FEATURE:
<223> OTHER INFORMATION: Probe for LCR, wildtype-specific, reverse
      strand

<400> SEQUENCE: 6
caaggacaaa atacctgtat tcctc                                              25

<210> SEQ ID NO 7
<211> LENGTH: 25
<212> TYPE: DNA
<213> ORGANISM: Artificial Sequence
<220> FEATURE:
<223> OTHER INFORMATION: Probe for LCR, mutation-specific, reverse
      strand

<400> SEQUENCE: 7
caaggacaaa atacctgtat tcctt                                              25

<210> SEQ ID NO 8
<211> LENGTH: 17
<212> TYPE: DNA
<213> ORGANISM: Artificial Sequence
<220> FEATURE:
<223> OTHER INFORMATION: Probe for LCR, unspecific, 5' end
      phosphorylated, forward strand

<400> SEQUENCE: 8
gcctgtccag ggatctg                                                       17

<210> SEQ ID NO 9
<211> LENGTH: 51
<212> TYPE: DNA
<213> ORGANISM: Artificial Sequence
<220> FEATURE:
<223> OTHER INFORMATION: Linker probe for adapted LCR,
      wildtype-specific, 5' end phosphorylated, forward strand

<400> SEQUENCE: 9
aggaatacag gtattttgtc cttgattttt ttttagatcc ctggacaggc g                 51

<210> SEQ ID NO 10
<211> LENGTH: 51
<212> TYPE: DNA
<213> ORGANISM: Artificial Sequence
<220> FEATURE:
```

-continued

```
<223> OTHER INFORMATION: Linker probe for adapted LCR,
      wildtype-specific, 5' end phosphorylated, reverse strand

<400> SEQUENCE: 10
gcctgtccag ggatctgttt tttttcaag gacaaaatac ctgtattcct c          51

<210> SEQ ID NO 11
<211> LENGTH: 51
<212> TYPE: DNA
<213> ORGANISM: Artificial Sequence
<220> FEATURE:
<223> OTHER INFORMATION: Linker probe for adapted LCR,
      mutation-specific, 5' end phosphorylated, forward strand

<400> SEQUENCE: 11
aggaatacag gtattttgtc cttgattttt ttttagatcc ctggacaggc a         51

<210> SEQ ID NO 12
<211> LENGTH: 51
<212> TYPE: DNA
<213> ORGANISM: Artificial Sequence
<220> FEATURE:
<223> OTHER INFORMATION: Linker probe for adapted LCR,
      mutation-specific, 5' end phosphorylated, reverse strand

<400> SEQUENCE: 12
gcctgtccag ggatctgttt tttttcaag gacaaaatac ctgtattcct t          51
```